(12) United States Patent
Perschbacher et al.

(10) Patent No.: US 11,382,552 B2
(45) Date of Patent: Jul. 12, 2022

(54) REDUCING FALSE ALARMS IN CARDIAC MONITORING DEVICES

(71) Applicant: Cardiac Pacemakers, Inc., St. Paul, MN (US)

(72) Inventors: David L. Perschbacher, Coon Rapids, MN (US); Sunipa Saha, Shoreview, MN (US); Deepa Mahajan, North Oaks, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 166 days.

(21) Appl. No.: 16/042,296

(22) Filed: Jul. 23, 2018

(65) Prior Publication Data

US 2019/0029552 A1    Jan. 31, 2019

Related U.S. Application Data

(60) Provisional application No. 62/537,090, filed on Jul. 26, 2017.

(51) Int. Cl.
*A61B 5/316* (2021.01)
*A61N 1/37* (2006.01)
(Continued)

(52) U.S. Cl.
CPC .............. *A61B 5/316* (2021.01); *A61B 5/287* (2021.01); *A61N 1/3702* (2013.01);
(Continued)

(58) Field of Classification Search
CPC .............. A61B 5/04018; A61B 5/0422; A61B 5/04014; A61B 5/0464; A61B 5/04525; A61B 5/0456; A61B 5/686; A61B 5/046; A61B 5/316; A61B 5/287; A61B 5/35; A61B 5/352; A61B 5/361; A61B 5/363;
(Continued)

(56) References Cited

U.S. PATENT DOCUMENTS

| | | | | |
|---|---|---|---|---|
| 4,023,564 A | * | 5/1977 | Valiquette | A61B 5/04525 600/517 |
| 5,545,186 A | * | 8/1996 | Olson | A61B 5/042 607/14 |

(Continued)

*Primary Examiner* — Gary Jackson
*Assistant Examiner* — Sebastian X Lukjan
(74) *Attorney, Agent, or Firm* — Schwegman Lundberg & Woessner, P.A.

(57) ABSTRACT

An apparatus comprises an arrhythmia detection circuit configured to: receive a cardiac signal representative of cardiac activity of a subject; apply a first arrhythmia detection criteria to the received cardiac signal; apply, in response to the applied first arrhythmia detection criteria producing a positive indication of arrhythmia, a second arrhythmia detection criteria to the received cardiac signal, wherein the second arrhythmia detection criteria is more specific to detection of arrhythmia than the first detection criteria; detect, in response to the applied first and second arrhythmia detection criteria, a sensing event indicating one or both of the first and second arrhythmia detection criteria are susceptible to false indications of arrhythmia; and adjust, in response to a detected sensing event, sensitivity or specificity of one or both of the first and second arrhythmia detection criteria.

20 Claims, 8 Drawing Sheets

(51) Int. Cl.
    *A61N 1/39*     (2006.01)
    *A61B 5/287*     (2021.01)
    *A61B 5/00*     (2006.01)
    *A61N 1/362*     (2006.01)
    *A61N 1/365*     (2006.01)
    *A61B 5/35*     (2021.01)
    *A61B 5/352*     (2021.01)
    *A61B 5/361*     (2021.01)
    *A61B 5/363*     (2021.01)

(52) U.S. Cl.
    CPC ............ *A61N 1/39622* (2017.08); *A61B 5/35* (2021.01); *A61B 5/352* (2021.01); *A61B 5/361* (2021.01); *A61B 5/363* (2021.01); *A61B 5/686* (2013.01); *A61N 1/365* (2013.01); *A61N 1/3624* (2013.01); *A61N 1/395* (2013.01); *A61N 1/3987* (2013.01)

(58) Field of Classification Search
    CPC .. A61N 1/39622; A61N 1/3702; A61N 1/365; A61N 1/3624; A61N 1/395; A61N 1/3987
    See application file for complete search history.

(56) References Cited

U.S. PATENT DOCUMENTS

| | | | |
|---|---|---|---|
| 2004/0215091 A1* | 10/2004 | Lohman | A61B 5/046 600/515 |
| 2004/0254611 A1* | 12/2004 | Paireddy | A61B 5/04525 607/4 |
| 2007/0078356 A1* | 4/2007 | Faber | A61N 1/3962 600/518 |
| 2013/0109985 A1* | 5/2013 | Gillberg | A61B 5/0464 600/509 |
| 2013/0197380 A1* | 8/2013 | Oral | A61B 5/0452 600/518 |
| 2014/0088660 A1* | 3/2014 | Debardi | A61N 1/3993 607/7 |
| 2015/0297104 A1* | 10/2015 | Chen | A61B 5/044 600/377 |
| 2016/0235317 A1* | 8/2016 | Sarkar | A61N 1/36507 |
| 2016/0331257 A1* | 11/2016 | Baumann | A61B 5/25 |
| 2016/0331985 A1* | 11/2016 | Allavatam | A61N 1/3925 |
| 2017/0027464 A1* | 2/2017 | Cole | A61B 5/0452 |
| 2018/0035956 A1* | 2/2018 | Gunderson | A61B 5/747 |

* cited by examiner

United States Patent US 11,382,552 B2

REDUCING FALSE ALARMS IN CARDIAC MONITORING DEVICES

CLAIM OF PRIORITY

This application claims the benefit of priority under 35 U.S.C. § 119(e) of U.S. Provisional Patent Application Ser. No. 62/537,090, filed on Jul. 26, 2017, which is herein incorporated by reference in its entirety.

BACKGROUND

Ambulatory medical devices include implantable medical devices (IMDs), wearable medical devices, handheld medical devices, and other medical devices. Some examples of IMDs include cardiac function management (CFM) devices such as implantable pacemakers, implantable cardioverter defibrillators (ICDs), subcutaneous implantable cardioverter defibrillators (S-ICDs), cardiac resynchronization therapy devices (CRTs), and devices that include a combination of such capabilities. The devices can be used to treat patients or subjects using electrical or other therapy, or to aid a physician or caregiver in patient diagnosis through internal monitoring of a patient's condition.

Some implantable medical devices can be diagnostic-only devices, such as implantable loop recorders (ILRs), subcutaneously insertable cardiac monitors (ICMs), and subcutaneously insertable heart failure monitors (SubQ HFMs). The devices may include electrodes in communication with one or more sense amplifiers to monitor electrical heart activity within a patient, or can include one or more sensors to monitor one or more other patient parameters. Subcutaneously implantable devices may include electrodes that are able to sense cardiac signals without being in direct contact with the patient's heart. Other examples of IMDs include implantable drug delivery systems or implantable devices with neural stimulation capability (e.g., vagus nerve stimulator, baroreflex stimulator, carotid sinus stimulator, spinal cord stimulator, deep brain stimulator, etc.).

Some examples of wearable medical devices include wearable cardioverter defibrillators (WCDs) and wearable diagnostic devices (e.g., an ambulatory monitoring vest, holter monitor, cardiac event monitor, or mobile cardiac telemetry devices). WCDs can be monitoring devices that include surface electrodes. The surface electrodes may be arranged to provide one or both of monitoring to provide surface electrocardiograms (ECGs) and delivery of cardioverter and defibrillator shock therapy. In some examples, a wearable medical device can also include a monitoring patch worn by the patient such as an adherable patch or can be included with an article of clothing worn by the patient.

Some examples of handheld medical devices include smartphones and personal data assistants (PDAs). The handheld devices can be diagnostic devices that record an electrocardiograph (ECG) or other physiological parameter while the device is resting in the patient's hand or being held to the patient's chest.

Device-based patient monitoring and diagnostics can generate false alarms. The monitoring device may incorrectly classify events and generate a false positive that the patient experienced a physiological event. False alarms can lead to unnecessary work by clinicians such as reviewing recordings made by the device to analyze and determine the true events that occurred for the patient. This extra work can lead to increased cost associated with the device-based monitoring and can result in reduced patient satisfaction with the device.

OVERVIEW

It can be desirable for ambulatory medical devices to correctly detect and identify cardiac arrhythmias. This can help to provide the most effective device-based therapy (e.g., electrical stimulation therapy) or non-device based therapy (e.g., drug therapy) for the patient. The present subject matter relates to improving device-based detection or classification of cardiac arrhythmia.

Example 1 can include subject matter (such as an apparatus) comprising an arrhythmia detection circuit configured to: receive a cardiac signal representative of cardiac activity of a subject; apply one or more first arrhythmia detection criteria to the received cardiac signal; apply one or more second arrhythmia detection criteria to the sensed cardiac signal in response to the applied first arrhythmia detection criteria producing a positive indication of arrhythmia, wherein the second arrhythmia detection criteria are more specific to detection of arrhythmia than the first detection criteria; detect a sensing event indicating one or both of the first and second arrhythmia detection criteria are susceptible to false indications of arrhythmia; and adjust, in response to a detected sensing event, sensitivity or specificity of one or both of the first and second arrhythmia detection criteria.

In Example 2, the subject matter of Example 1 optionally includes a arrhythmia detection circuit configured to adjust the sensitivity or specificity for one or both of the first and second arrhythmia detection criteria in response to detection of one or both of a heart rate that is non-physiologically fast, and a specified number of noise hits in sensing of the cardiac signal that occur within a specified time duration.

In example 3, the subject matter of one or both of Examples 1 and 2 optionally includes an arrhythmia detection circuit configured to adjust the sensitivity or specificity for one or both of the first and second arrhythmia detection criteria in response to detection of a cardiac rhythm for which one or both of the first and second arrhythmia detection criteria are susceptible to false alarms.

In Example 4, the subject matter of one or any combination of Examples 1-3 optionally includes an arrhythmia detection circuit configured to adjust the sensitivity or specificity for one or both of the first and second arrhythmia detection criteria in response to detecting one or more of a number of pauses in cardiac depolarization in the received cardiac signal that exceeds a specified threshold number of pauses, a heart rate that is non-physiologically slow, and a number of changes in amplitude of the received cardiac signal that exceed a specified amplitude change threshold within a specified period of time.

In Example 5, the subject matter of one or any combination of Examples 1-4 optionally includes an arrhythmia detection circuit configured to detect atrial tachyarrhythmia using the first and second arrhythmia detection criteria; adjust a detection threshold of one or both of the first and second arrhythmia detection criteria to change sensitivity or specificity to atrial tachyarrhythmia detection in response to detection of the sensing event, and restore the detection threshold to an original sensitivity or specificity when the detected sensing event ceases to be detected for a specified period of time.

In Example 6, the subject matter of one or any combination of Examples 1-5 optionally includes an arrhythmia detection circuit configured to detect atrial flutter (AF) using the first and second detection criteria, wherein the first and second arrhythmia detection criteria include one or more of: detection that sensed ventricular depolarization intervals (V-V intervals) satisfy a specified V-V interval scatter AF detection threshold, detection that sensed V-V intervals satisfy a specified V-V interval double decrement AF detection threshold, and detection that sensed V-V intervals satisfy a specified Wenckebach AF detection threshold.

In Example 7, the subject matter of one or any combination of Examples 1-6 optionally includes an arrhythmia detection circuit configured to: detect ventricular tachyarrhythmia using the first and second detection criteria; adjust a detection threshold of one or both of the first and second arrhythmia detection criteria to change sensitivity or specificity to ventricular tachyarrhythmia detection in response to detection of the sensing event; and restore the detection threshold to an original sensitivity or specificity when the detected sensing event ceases to be detected for a specified period of time.

In Example 8, the subject matter of Example 7 optionally includes a therapy circuit configured to provide defibrillation shock therapy to the subject; and a control circuit configured to initiate delivery of the defibrillation shock therapy in response to the detection of the ventricular tachyarrhythmia.

In Example 9, the subject matter of one or any combination of Examples 1-8 optionally includes an arrhythmia detection circuit configured to: detect bradycardia using the first and second arrhythmia detection criteria; adjust a detection threshold of one or both of the first and second detection criteria to change sensitivity or specificity to bradycardia detection in response to detection of the sensing event; and restore the detection thresholds to an original specificity when the detected sensing event ceases to be detected for a specified period of time.

In Example 10, the subject matter of Example 9 optionally includes a therapy circuit configured to provide electrical pacing therapy to the subject; and a control circuit configured to initiate delivery of the electrical pacing therapy according to a first pacing therapy mode; and change the pacing therapy mode according to the detected cardiac arrhythmia.

In Example 11, the subject matter of one or any combination of Examples 1-10 optionally includes an arrhythmia detection circuit configured to continue to adjust the sensitivity or specificity for one or both of the first and second arrhythmia detection criteria when continuing to detect the sensing event, and restore original sensitivity or specificity to the first and second arrhythmia detection criteria when the detected sensing event ceases to be detected for a specified period of time.

Example 12 includes subject matter (such as a method of controlling operation of an arrhythmia detection circuit, a means for performing acts, or a machine-readable medium including instructions that, when performed by the machine, cause the machine to perform acts), or can optionally be combined with one or any combination of Examples 1-11 to include such subject matter, comprising receiving a cardiac signal representative of cardiac activity of a subject at the arrhythmia detection circuit; applying one or more first arrhythmia detection criteria to the received cardiac signal using the arrhythmia detection circuit; applying, in response to the applied first arrhythmia detection criteria producing a positive indication of arrhythmia, one or more second arrhythmia detection criteria to the received cardiac signal, wherein the second arrhythmia detection criteria are more specific to detection of the arrhythmia than the first detection criteria; detecting, using the arrhythmia detection circuit, a sensing event indicating one or both of the first and second arrhythmia detection criteria are susceptible to false indications of arrhythmia; and adjusting, in response to a detected sensing event, sensitivity or specificity of one or both of the first and second arrhythmia detection criteria using the arrhythmia detection circuit.

In Example 13, the subject matter of Example 12 optionally includes detecting a specified number of noise hits in the sensing of the cardiac signal within a specified time duration, and detecting a heart rate that is non-physiologically fast.

In Example 14, the subject matter of one or both of Examples 12 and 13 optionally includes detecting a cardiac rhythm for which one or both of the first and second detection criteria are susceptible to false alarms.

In Example 15, the subject matter of one or any combination of Examples 12-14 optionally includes one or more of detecting a number of pauses in cardiac depolarization in the sensed cardiac signal, detecting a heart rate that is non-physiologically slow, and sensing a specified number of changes in amplitude of the sensed cardiac signal that exceed a specified amplitude change threshold within a specified period of time.

In Example 16, the subject matter of one or any combination of Examples 12-15 optionally includes first and second arrhythmia detection criteria that detect atrial tachyarrhythmia, wherein the adjusting sensitivity or specificity includes adjusting an atrial tachyarrhythmia detection threshold of one or both of the first and second arrhythmia detection criteria, and wherein the method further includes restoring the atrial tachyarrhythmia detection threshold to an original sensitivity or specificity when the detected sensing event ceases to be detected for a specified period of time.

In Example 17, the subject matter of one or any combination of Examples 12-16 optionally includes first and second arrhythmia detection criteria that detect ventricular tachyarrhythmia, wherein the adjusting sensitivity or specificity includes adjusting a ventricular tachyarrhythmia detection threshold of one or both of the first and second arrhythmia detection criteria, and wherein the method further includes restoring the ventricular tachyarrhythmia detection threshold to an original sensitivity or specificity when the detected sensing event ceases to be detected for a specified period of time.

Example 18 includes subject matter (such as a system), or can optionally be combined with one or any combination of Examples 1-17 to include such subject matter, comprising: a sensing circuit configured to provide a sensed ventricular cardiac signal of a subject when operatively coupled to electrodes that contact a subject; and an arrhythmia detection circuit operatively coupled to the sensing circuit and configured to: apply one or more first atrial arrhythmia detection criteria to the sensed ventricular cardiac signal; apply one or more second atrial arrhythmia detection criteria to the sensed ventricular cardiac signal in response to the applied first arrhythmia detection criteria producing a positive indication of atrial arrhythmia, wherein the second arrhythmia detection criteria are more specific to detection of atrial arrhythmia than the first detection criteria; detect a sensing event indicating one or both of the first and second arrhythmia detection criteria are susceptible to false indications of arrhythmia; and adjust, in response to a detected sensing event, sensitivity or specificity of one or both of the first and second arrhythmia detection criteria.

In Example 19, the subject matter of Example 18 optionally includes an arrhythmia detection circuit configured to detect atrial flutter (AF) using the first and second atrial arrhythmia detection criteria, adjust a detection threshold of one or both of the first and second detection criteria to change sensitivity or specificity to AF in response to detection of the sensing event, and restore the detection threshold to an original sensitivity or specificity when the detected sensing event ceases to be detected for a specified period of time.

In Example 20, the subject matter of one or both of claims 18 and 19 optionally includes an arrhythmia detection circuit is configured to: confirm AF using the second atrial arrhythmia detection criteria when sensed ventricular depolarization intervals (V-V intervals) satisfy one or more of a specified V-V interval scatter AF detection threshold, a specified V-V interval double decrement AF detection threshold, and a specified Wenckebach AF detection threshold; and change the sensitivity or specificity of the one or more of the V-V interval scatter AF detection threshold, the V-V interval double decrement AF detection threshold, and the Wenckebach AF detection threshold in response to detection of the sensing event.

Example 21 can include, or can optionally be combined with any portion or combination of any portions of any one or more of Examples 1-22 to include, subject matter that can include means for performing any one or more of the functions of Examples 1-20, or a machine-readable medium including instructions that, when performed by a machine, cause the machine to perform any one or more of the functions of Examples 1-20.

These non-limiting examples can be combined in any permutation or combination. This section is not intended to provide an exclusive or exhaustive explanation of the invention. The detailed description is included to provide further information about the present patent application such as a discussion of the dependent claims and the interrelation of the dependent and independent claims.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, the various examples discussed in the present document.

DETAILED DESCRIPTION

An ambulatory medical device can include one or more of the features, structures, methods, or combinations thereof described herein. For example, a cardiac monitor or a cardiac stimulator may be implemented to include one or more of the advantageous features or processes described below. It is intended that such a monitor, stimulator, or other ambulatory device need not include all of the features described herein, but may be implemented to include selected features that provide for unique structures or functionality. Such a device may be implemented to provide a variety of therapeutic or diagnostic functions.

Figure 1:
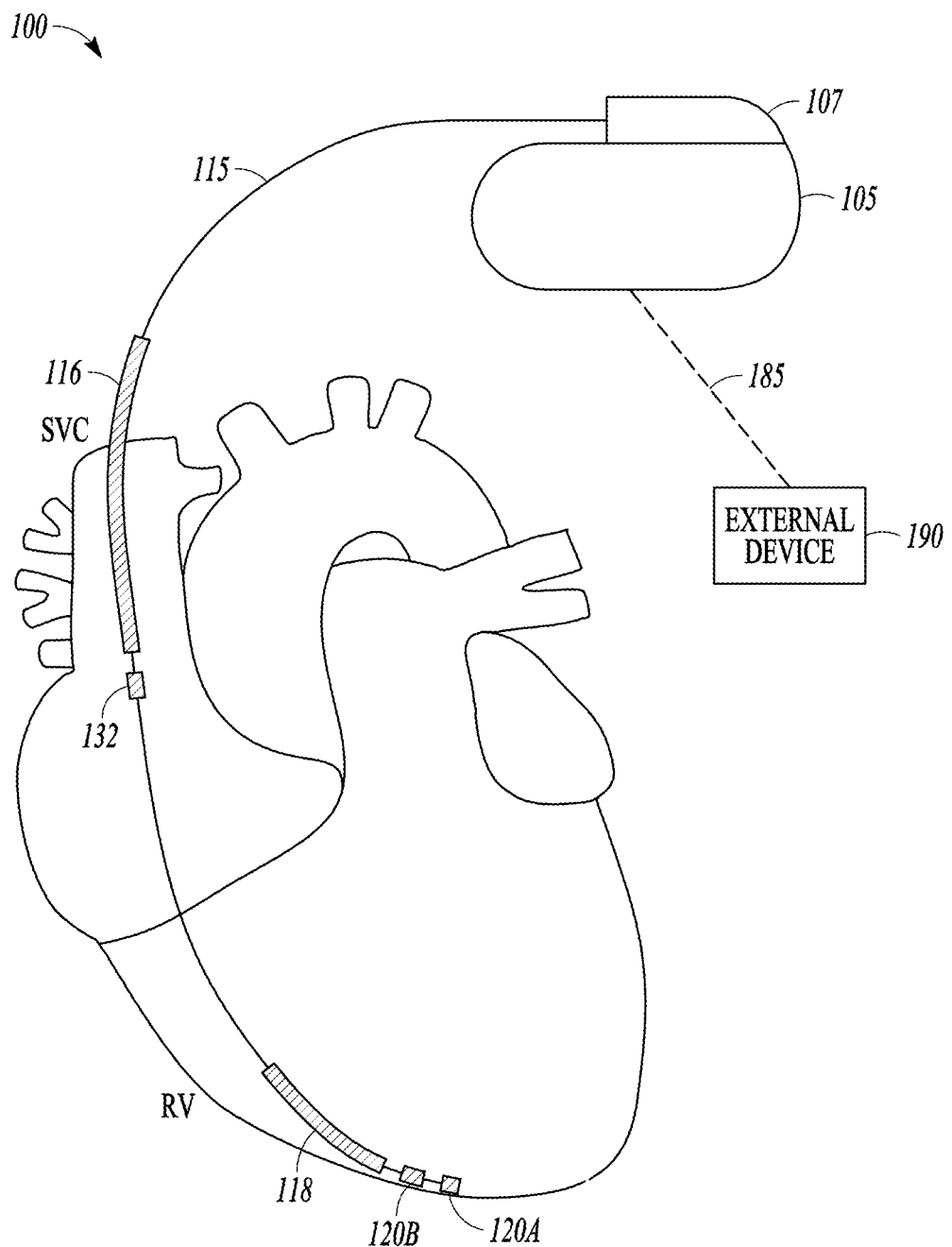
FIG. 1 is an illustration of an example of portions of a medical device system that includes an ambulatory medical device.

FIG. 1 is an illustration of an example of portions of a system 100 that includes an ambulatory medical device that is an IMD 105. Examples of the IMD 105 include, without limitation, a pacemaker, a cardioverter, a defibrillator, and other cardiac monitoring and therapy delivery devices, including cardiac devices that include or work in coordination with one or more neuro-stimulating devices, drugs, drug delivery systems, or other therapies. In an example, the system 100 shown is used to treat cardiac arrhythmias. The IMD 105 typically includes an electronics unit coupled by one or more cardiac leads 115 to a heart of a patient or subject. The electronics unit of the IMD 105 typically includes components that are enclosed in a hermetically-sealed housing sometimes referred to as a canister or "can." The system 100 also typically includes an IMD programmer or other external system 190 that communicates one or more wireless signals 185 with the IMD 105, such as by using radio frequency (RF) or by one or more other telemetry methods.

The example shown includes a right ventricular (RV) lead 115 having a proximal end and a distal end. The proximal end is coupled to a header connector 107. The distal end is configured for placement in the RV. The RV lead 115 can include one or more of a proximal defibrillation electrode 116, a distal defibrillation electrode 118 (e.g., RV Coil), an RV tip electrode 120A, and an RV ring electrode 120B. The defibrillation electrode 116 is generally incorporated into the lead body such as in a location suitable for supraventricular placement in the superior vena cava (e.g., SVC Coil). In some examples, the RV lead 115 includes a ring electrode 132 (e.g., SVC ring) in the vicinity of the proximal defibrillation electrode 116. The defibrillation electrode 118 is incorporated into the lead body near the distal end, such as for placement in the RV. The RV electrodes 120A and 120B can form a bipolar electrode pair and are generally incorporated into the lead body at the lead distal end. The electrodes 116, 118, 120A, and 120B are each electrically coupled to IMD 105, such as through one or more conductors extending within the lead body. The proximal defibrillation electrode 116, distal defibrillation electrode 118, or an electrode formed on the can of IMD 105 allow for delivery of cardioversion or defibrillation pulses to the heart. The RV tip electrode 120A, RV ring electrode 120B, or an electrode formed on the can of IMD 105 allow for sensing an RV electrogram signal representative of RV depolarizations and delivering RV pacing pulses. The IMD 105 includes a sense amplifier circuit to provide amplification or filtering of the sensed signal. Sensing and pacing allows the IMD 105 to adjust timing of the heart chamber contractions. The IMD example shown in FIG. 1 may not include any electrodes for sensing electrical activity in an atrium.

Figure 2:
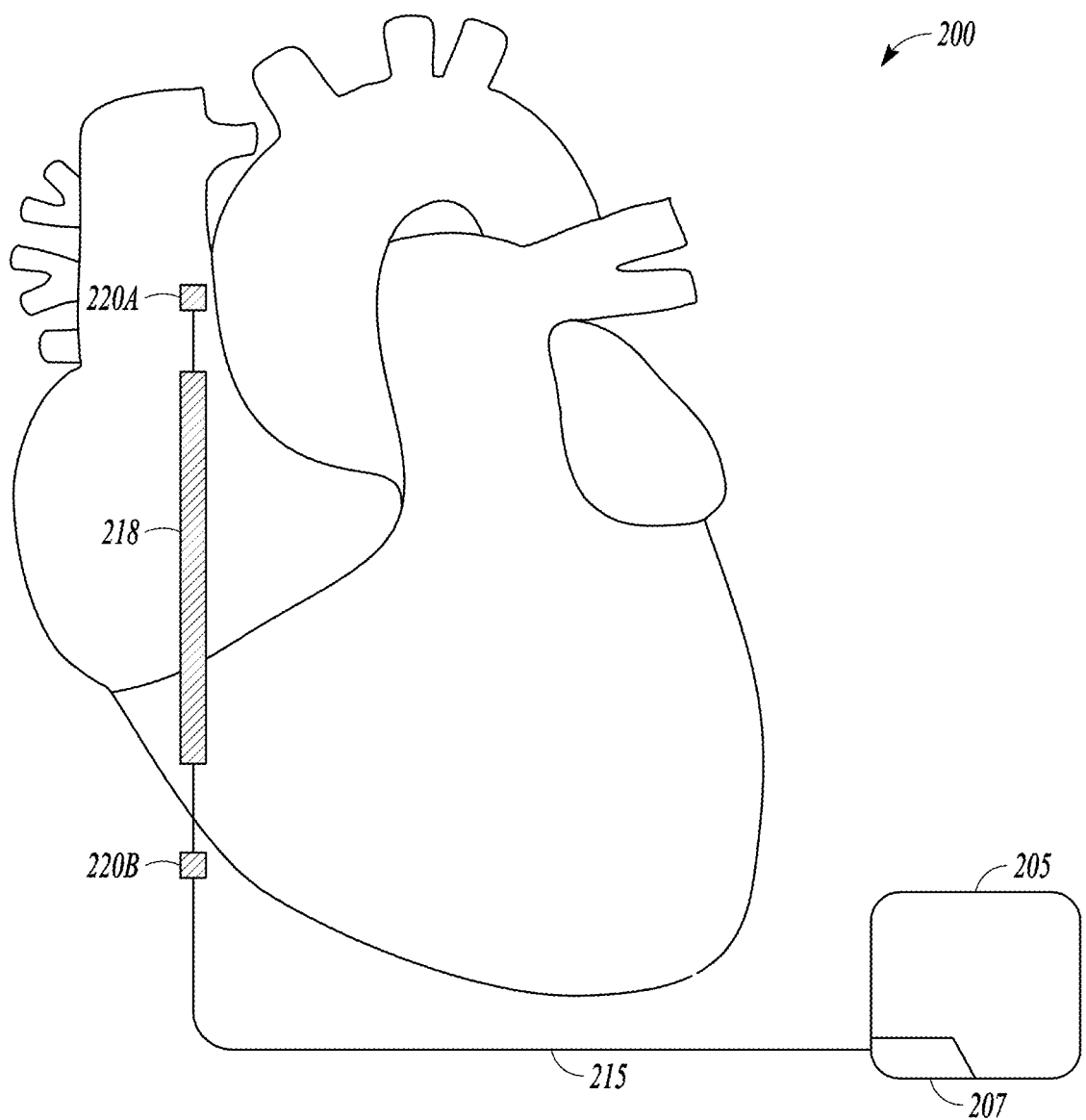
FIGS. 2 and 3 are illustrations of further examples of ambulatory medical devices.

FIG. 2 is an illustration of an example of portions of a system 200 that includes an S-ICD 205. The S-ICD 205 is implantable subcutaneously and includes a lead 215. The lead 215 is implanted subcutaneously and the proximal end of the lead 215 is coupled to a header connector 207. The lead 215 can include electrode 220A and electrode 220B to sense ventricular depolarization (e.g., using far-field sensing), but in the example illustrated, the lead does not include any electrodes that directly contact the heart. The lead 215 includes a defibrillation electrode 218 that may be a coil electrode. The S-ICD 205 may provide one or more of cardioversion therapy and defibrillation high energy shock therapy to the heart using the defibrillation electrode 218 and an electrode formed on the can of the S-ICD 205. In some examples, the S-ICD 205 may also provide pacing pulses for anti-tachycardia therapy or bradycardia therapy. Note that atrial leads are not provided in the arrangement of the electrodes, but electrodes 220A and 220B allow for sensing a far-field ventricular electrogram signal. The S-ICD 205 can use intrinsic cardiac signals sensed with the ventricular electrode for arrhythmia detection and discrimination (e.g., by rate sensing and/or depolarization signal morphology analysis).

Figure 3:
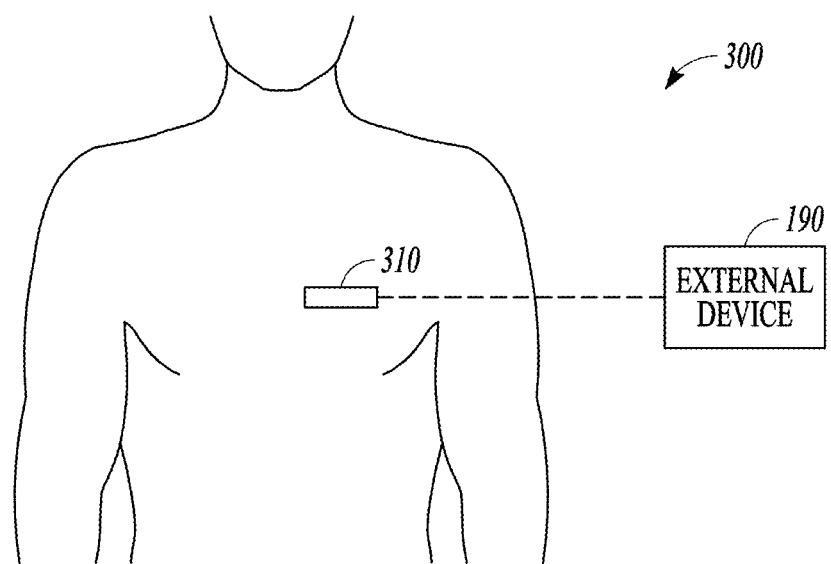

FIG. 3 is an illustration of an example of a system 300 that includes an insertable medical device 310 such as an insertable cardiac monitor (ICM) and external device 190. The ICM may be a diagnostic-only device inserted subcutaneously to sense electrical signals of the heart and, depending on the device, other signals of the heart. The ICM may include two or more electrodes on the housing and/or header of the device to sense the electrical signals of the heart. In some examples, no electrodes are arranged in or on the heart.

Figure 4:
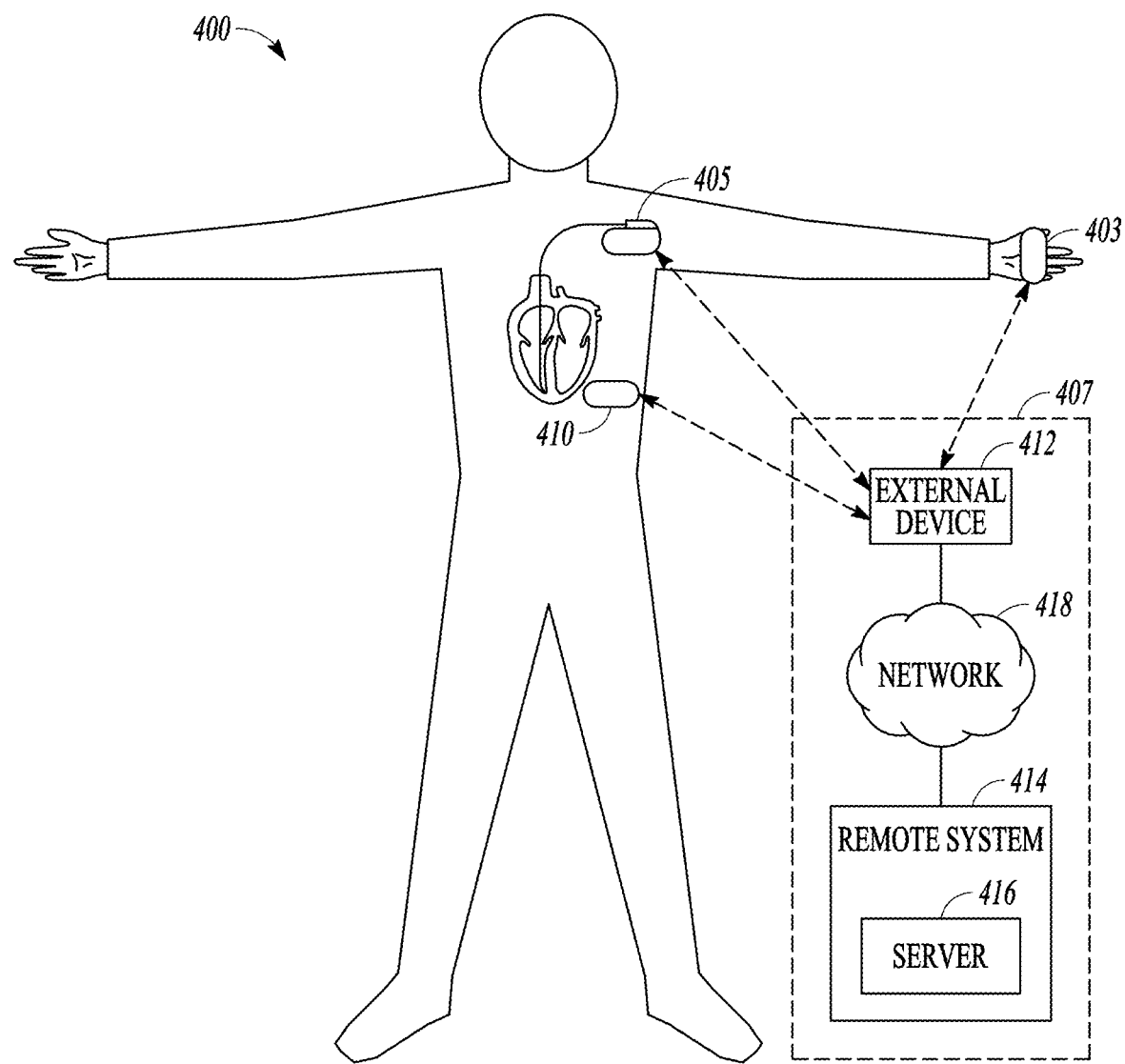
FIG. 4 is an illustration of portions of another example of a medical device system.

FIG. 4 is an illustration of portions of another example of a medical device system 400. The system 400 may include one or more ambulatory medical devices, such as a conventionally implantable or subcutaneously implantable medical device 405, an insertable medical device 410, a wearable medical device, or a handheld medical device 403, or any other medical device described herein. One or more of the medical devices can include a communication circuit (e.g., a telemetry circuit) to communicate an indication of cardiac arrhythmia (e.g., AF) to a communication system 407. The communication system 407 can include an external communication device 412 and a remote system 414 that communicates with the external communication device 412 via a network 418 (e.g., the internet, a proprietary computer network, or a cellular phone network). The remote system 414 may include a server 416 remotely located from the external communication device 412 and the subject to perform further processing of the cardiac data or other patient management functions. The external communication device 412 may include a programmer to program parameters of the implantable medical device. One or both of the external communication device 412 and the remote system 414 may include a display to present the indication of arrhythmia to a user, such as a clinician.

Device-based diagnostics can produce false alarms, such as a false positive alert for a condition that is incorrectly detected by the monitoring device. False alarms cause extra work for clinicians in that device-based recordings of the episode producing the false alarms need to be reviewed. This extra work diminishes the benefit of the automaticity of the monitoring device. Detection algorithms that use static detection criteria are prone to repeat the misdiagnosis of an event and may repeat the reporting of false alarms.

Figure 5A:
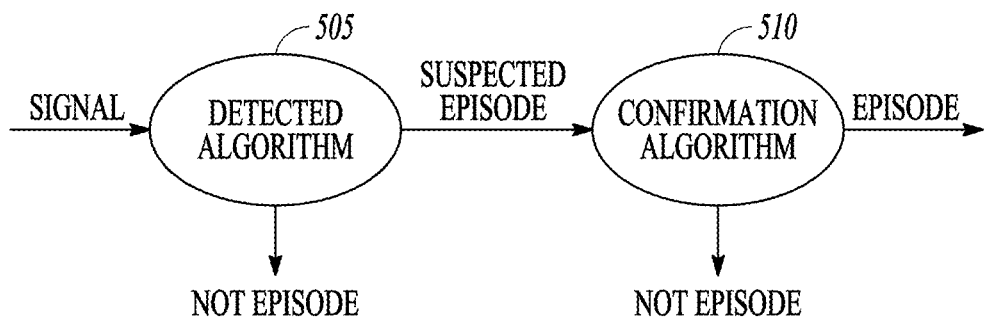
FIG. 5A shows an example of a flow diagram for static detection of a patient condition using an ambulatory medical device.

FIG. 5A shows an example of a flow diagram for static detection of a patient condition by a medical device. As an example, the medical device may detect episodes of cardiac arrhythmia of the patient. The detection is static in that the same detection criteria is unchanged once they are programmed into the device. In FIG. 5A<a first detection algorithm 505 is used as a first tier of detection. The result of the first detection algorithm is either an indication that no episode of the patient condition is suspected or an indication that an episode is suspected. If an episode is suspected, a second confirmation algorithm 510 is then used as a second tier of detection to confirm the result of the first detection algorithm. The first detection algorithm 505 can involve a lower amount of signal processing by the monitoring device than the second criteria. If there is a positive indication from the first detection algorithm 505, the additional signal processing of the second confirmation algorithm may be used to confirm the suspected episode. The two-tiered approach of FIG. 5A can reduce the amount of battery power needed for the overall monitoring of the patient.

Certain situations may be more likely to lead to incorrect results of the monitoring of the patient condition. For example, periods of signal noise picked up by sensing circuits of the device may be interpreted as physiological events. This can be referred to as oversensing and may lead to a misclassification by the device. In another example, sudden changes in signal amplitude may cause the monitoring device to miss detecting certain events. For instance, a shift in posture of the patient may lead to sudden changes in amplitude of signals sensed using the sensing circuits of the monitoring device. Some monitoring devices use dynamic sensing thresholds that may change a detection threshold when signals with different amplitudes are encountered. The threshold is automatically changed to avoid oversensing of one or both of T-waves and P-waves associated with the larger amplitude signals, and may be changed to avoid undersensing of smaller R-waves if the change in signal amplitude is due to an event such as a change in posture of the patient.

In a further example, the monitoring device may sense electrical cardiac activity signals to detect and classify cardiac events of the patient such as episodes of cardiac arrhythmia. Some cardiac rhythms may confound the identification of cardiac arrhythmia. For example, periods of premature ventricular contractions (PVCs), premature atrial contractions (PACs), Wenckebach rhythms, or sinus tachycardia may fool device-based cardiac arrhythmia classification algorithms leading to incorrect classifications. Because the detection in FIG. 5A is static, long runs of false alarms may be generated by the device under conditions in which the algorithms are susceptible to false alarms.

Figure 5B:
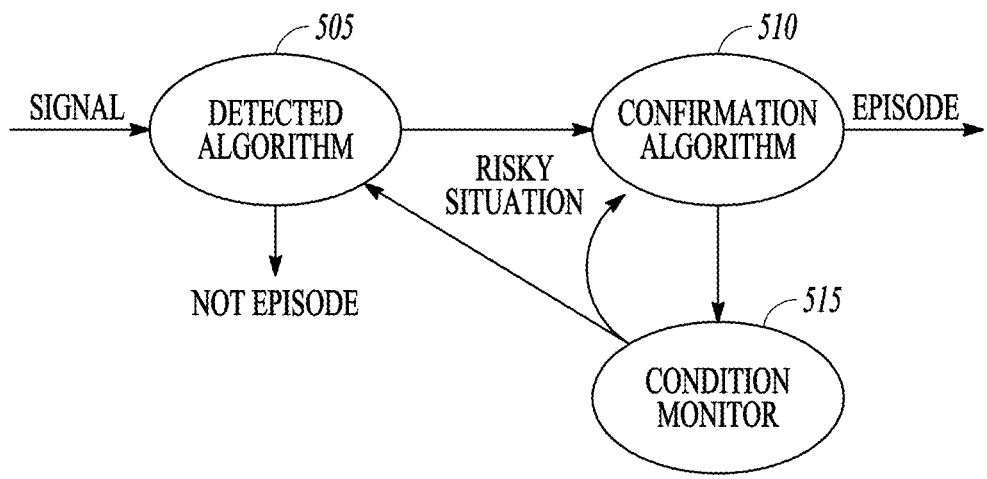
FIG. 5B shows an example of a flow diagram for dynamic detection of a patient condition using an ambulatory medical device.

FIG. 5B shows an example of a flow diagram of dynamic detection of the patient's condition by a medical device. The dynamic detection includes a detection algorithm 505 and a confirmation algorithm 510 as in FIG. 5A. The dynamic detection of FIG. 5B also includes algorithm monitoring 515 to determine conditions for sensing in which false positives are more likely. When conditions for false positives are present, one or both of the detection algorithm 505 and the confirmation algorithm are changed 510 automatically by the device.

The change to the algorithm may involve changing the sensitivity or the specificity of detecting the patient condition. If the medical device is to detect or treat abnormal cardiac rhythms, sensitivity can refer to the ability of the detection and confirmation schemes of the device to effectively detect an abnormal cardiac rhythm. Specificity can refer to the ability of the detection schemes to correctly identify heart rhythm that the device is not intended to detect or treat (e.g., normal rhythms, other types of arrhythmias, or noise mistakenly identified as cardiac arrhythmia). As an example, the specificity of the arrhythmia detection may be changed in the presence of noise to be more exclusive of possible arrhythmias to reduce false positives. The specificity of one or both of the detection algorithm and the confirmation algorithm of FIG. 5B may be changed based on the detected conditions. In another example, the sensitivity of one or both of the detection algorithm and the confirmation algorithm may be changed. In a further example, the sensitivity of either the detection algorithm or the confirmation algorithm may be changed, and the specificity of the other algorithm may be changed.

Figure 6:
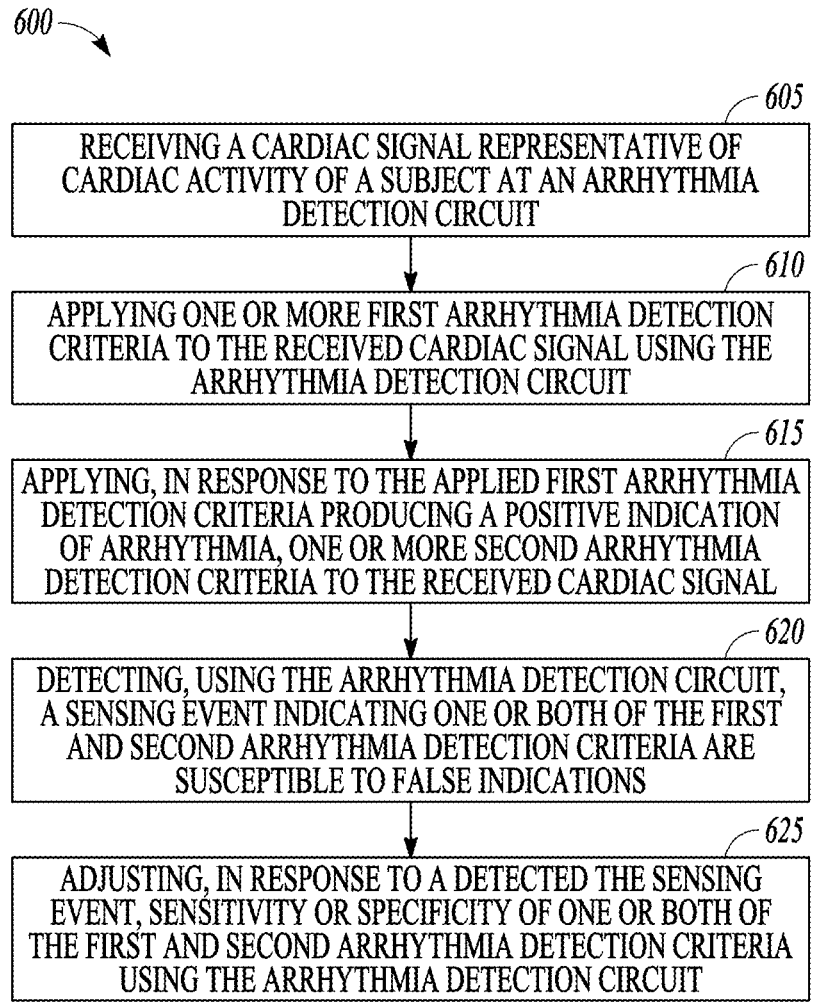
FIG. 6 is a flow diagram of an example of a method of operating an ambulatory medical device.

FIG. 6 is a flow diagram of an example of a method 600 of controlling operation of an ambulatory medical device system to detect cardiac arrhythmia. At 605, a cardiac signal representative of cardiac activity of a subject is received at an arrhythmia detection circuit of the ambulatory medical device. The cardiac signal may be produced using a sensing circuit of the ambulatory medical device, or the cardiac signal may be produced by a separate device and communicated to the ambulatory medical device.

At 610, one or more first arrhythmia detection criteria are applied to the received cardiac signal using the arrhythmia detection circuit. At 615, if applying the first detection criteria results in a positive indication for the arrhythmia, one or more second arrhythmia detection criteria are applied to the received cardiac signal. The second arrhythmia detection criteria are more specific to detection of the arrhythmia than the first detection criteria and may be used to confirm the result of the first arrhythmia detection criteria. As an illustrative example intended to be non-limiting, if the arrhythmia to be detected is ventricular tachycardia, the first detection criteria may include detecting a heart rate that exceeds a specified threshold (e.g., a threshold programmed into the device). The second detection criteria may include a morphology analysis that compares the received cardiac signal to a template representative of normal sinus rhythm (NSR) or ventricular tachycardia to confirm the ventricular tachycardia.

At 615, a sensing event is detected using the arrhythmia detection circuit. The sensing event may indicate a situation in which one or both of the first and second arrhythmia detection criteria are susceptible to false indications of arrhythmia. The sensing event may indicate that the medical device is prone to oversensing or undersensing of physiological events related to the cardiac arrhythmia. In another example, the sensing event may be the presence of a cardiac rhythm known to confound detection of cardiac arrhythmia.

In response to detecting the sensing event, the arrhythmia detection circuit takes corrective action. At 620, the arrhythmia detection circuit adjusts the sensitivity or the specificity of one or both of the first and second arrhythmia detection criteria. For example, if the arrhythmia detection circuit determines that the medical device is prone to oversensing, the specificity of one or both of the first and second detection algorithms may be increased to be more exclusive. In another example, if the arrhythmia detection circuit determines that the medical device is prone to undersensing, the sensitivity of one or both of the first and second detection algorithms may be increased to be more inclusive.

Figure 7:
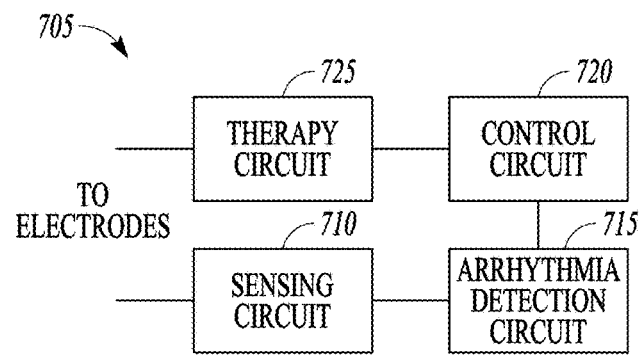
FIG. 7 shows a block diagram of portions of an example of an ambulatory medical device.

FIG. 7 is a block diagram of portions of an example of an ambulatory medical device 705. The device 705 includes a sensing circuit 710 and an arrhythmia detection circuit 715. The sensing circuit 710 may generate a sensed cardiac signal representative of cardiac activity of a subject. In certain examples, the sensing circuit 710 may be electrically coupled to one or more implantable electrodes included in a lead arranged for placement in a heart chamber. In certain examples, the sensing circuit 710 may be electrically coupled to one or more implantable electrodes included in a leadless implantable medical device. In certain examples, the sensing circuit 710 may be electrically coupled to one or more implantable electrodes configured to sense cardiac signals without direct cardiac contact with the subject (e.g., a subcutaneously implantable or insertable electrode).

The ambulatory medical device 705 may include a control circuit 720. The control circuit 720 may include a microprocessor, a digital signal processor, application specific integrated circuit (ASIC), or other type of processor, interpreting or executing instructions included in software or firmware. The arrhythmia detection circuit 715 may be integral to the control circuit 720 or may be separate from the control circuit 720.

To detect cardiac arrhythmia, the arrhythmia detection circuit 715 may apply a first arrhythmia detection criterion or criteria to the cardiac signal. In response to a positive indication of arrhythmia from the first arrhythmia detection criteria, the arrhythmia detection circuit 715 applies a second arrhythmia detection criteria to the cardiac signal that is more specific to detection of the arrhythmia than the first detection criteria. The arrhythmia detection circuit 715 also monitors for a sensing event that indicates that one or both of the first and second arrhythmia detection criteria are susceptible to false indications of arrhythmia.

The first arrhythmia detection criteria detects suspected arrhythmia events that are either confirmed or rejected by the second arrhythmia detection criteria. Too many rejections of suspected events detected by the first criteria may indicate risk of a false positive being detected. In some examples, when the second detection criteria rejects a number of suspected arrhythmia events that exceeds a specified threshold number within a specified period of time, the arrhythmia detection circuit 715 may increase a detection threshold of the first detection criteria to make it more difficult for the first detection criteria to produce a positive indication of the arrhythmia. As alternative, or in addition to, changing the first detection threshold, the arrhythmia detection circuit 715 may increase a detection threshold of the second detection criteria.

If the condition or situation that could lead to false alarms continues, the detection threshold of one or both of the first and second detection criteria could continue to be incrementally increased. The detection thresholds may be reset or gradually decremented back to the original values when the condition is no longer present to restore the original sensatory or specificity. The arrhythmia detection circuit 715 may determine that the condition that could lead to false alarms is no longer present when the first detection criteria does not identify a suspected episode for a specified period of time, or real episodes are not confirmed by the second detection criteria for a specified period of time.

According to some examples, the arrhythmia detection circuit 715 detects atrial tachyarrhythmia by applying the first and second arrhythmia detection criteria to a sensed cardiac signal. Atrial tachyarrhythmia includes atrial tachycardia (AT) and atrial flutter (AF). Some of the conditions that can result in false indications related to the detection of atrial tachyarrhythmia include oversensing by the sensing circuits, undersensing, and presence cardiac rhythms that confound the detection of AT or AF.

The arrhythmia detection circuit 715 may determine that oversensing by the sensing circuit 710 may be occurring when the device-determined heart rate of the patient or subject is non-physiologically fast. Non-physiologically fast means that the determined value of heart rate is not physiologically likely or possible. Oversensing may also be suspected when signal noise is detected in the cardiac signal. In certain examples, the ambulatory medical device includes a filter circuit (not shown) that detects noise. For instance, the filter circuit may be a high pass filter circuit having a corner frequency higher than any frequency of physiological interest. Artifacts in the filtered signal may indicate that sensing circuit includes a noise component (e.g., from electromagnetic interference (EMI) or a loose connection to a cardiac lead). In certain examples, the arrhythmia detection circuit 715 performs a morphology analysis of the sensed cardiac signal to detect noise. For instance, the arrhythmia detection circuit 715 may perform signal processing on the cardiac signal to determine a number of turns (i.e., change in direction) in the sensed signal. The arrhythmia detection circuit 715 determines the presence of noise in the cardiac signal when the number of turns exceeds a threshold number of turns within a specified period of time (e.g., within one second). In certain examples, the arrhythmia detection circuit 715 may monitor ventricular depolarization intervals (V-V intervals) in the sensed cardiac signal. The arrhythmia detection circuit 715 determines the presence of noise in the cardiac signal when the variability of V-V intervals exceeds a threshold variability value.

The arrhythmia detection circuit 715 may declare a "noise hit" when noise is detected using a filter circuit, using a morphological analysis, or by monitoring V-V interval variability. The arrhythmia detection circuit 715 may determine that oversensing is occurring when detecting a specified number of noise hits in the sensing of the cardiac signal that occur within a specified time duration. In response to determining the condition, the arrhythmia detection circuit 715 may adjust one or both of the first and second arrhythmia detection criteria.

Figure 8:
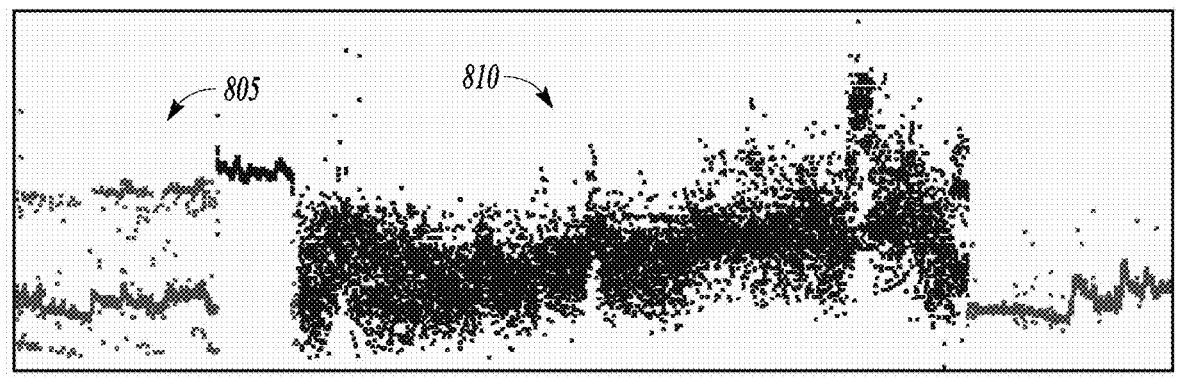
FIG. 8 shows an example of a sensed cardiac signal having both normal sinus rhythm and atrial fibrillation.

According to some examples, the arrhythmia detection circuit detects atrial tachyarrhythmia. In an illustrative example of dynamic detection, the first and second detection criteria may detect AF using ventricular depolarization (V-V) interval dispersion (sometimes referred to as scatter). FIG. 8 shows an example of a sensed physiological signal having a first region 805 corresponding to NSR and a second region 810 corresponding to AF. In the NSR region, the V-V intervals may be more regular and the differences in the V-V intervals will be small. In the AF region, the V-V intervals may be more disperse and the values of the differences in the V-V intervals may be more varied than for NSR. The arrhythmia detection circuit 715 may include a peak detector circuit to detect R-waves in the sensed physiological signal to determine V-V intervals. The arrhythmia detection circuit 715 may determine differences between the V-V intervals and determine a measure of V-V interval dispersion using the determined V-V interval differences. V-V intervals may be deemed more stable if the difference between successive V-V intervals is small. A larger difference may indicate V-V intervals are unstable.

In the example of FIG. 8, more of the V-V interval differences will be stable in the NSR region. In the AF region, the number of unstable V-V interval differences will increase relative to the number of stable V-V interval differences. Detecting AF may include determining a ratio using a number of stable interval differences and a number of unstable interval differences (e.g., ratio=unstable/stable). AF may be indicated when the ratio exceeds an AF detection threshold ratio. The threshold fraction or percentage can be lowered to make the detection more sensitive or raised to make the detection more specific for AF detection.

Either or both of the first and second arrhythmia detection criteria may use V-V interval dispersion to detect AF. Oversensing may lead to false positive indications of AF when using V-V interval dispersion to detect AF. In response to detecting an oversensing event, the arrhythmia detection circuit 715 may increase the threshold of the measure of V-V dispersion used to declare AF.

Figure 9:
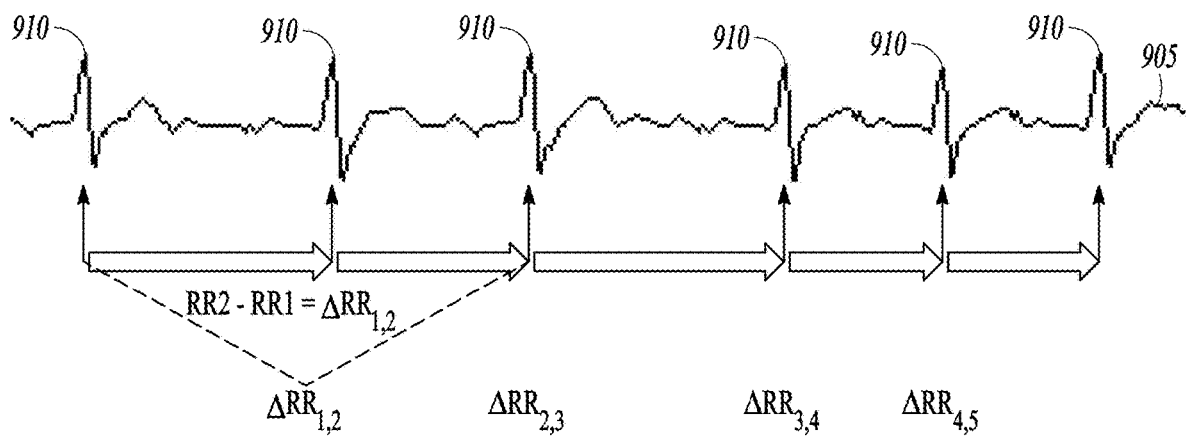
FIG. 9 shows another example of a sensed cardiac signal.

In another illustrative example of dynamic detection, the arrhythmia detection circuit 715 may detect AF using heart rate double decrement detection. FIG. 9 shows a representation of a sensed cardiac signal 905. The sensed signal is shown having a number of R-waves 910. The V-V intervals can be determined as intervals between the R-waves. RR1 in the Figure refers to the first interval between the first two R-waves; RR2 is the second interval between the second R-wave and the third R-wave, and so on. Differences between the V-V intervals are referred to $\Delta RR_{1,2}$ (e.g., the difference between the RR2 and RR1), $\Delta RR_{2,3}$ and so on. A heart rate double decrement event occurs when two consecutive V-V intervals occur in which the interval increases in both intervals (corresponding to a decrease or decrement in heart rate).

In the example of FIG. 9, if RR1 is 857 ms and RR2 is 1000 ms, a double decrement event occurs if the next interval RR3 is greater than 1000 ms (e.g., 1090 ms). If RR3 is less than 1000 ms, the V-V interval did not increase in two consecutive V-V intervals and a double decrement event did not occur. AF may be detected when the number of double decrement events exceeds a specified fraction or percentage of the intervals. The threshold fraction or percentage can be lowered to make the detection more sensitive or raised to make the detection more specific for AF detection. In response to detecting an oversensing event, the arrhythmia detection circuit 715 may increase the threshold for detection of heart rate double decrementing.

In another illustrative example of dynamic detection, either or both of the first and second detection criteria may detect AF when sensed V-V intervals satisfy a specified V-V interval Wenkebach threshold. Wenkebach detection involves an analysis of how truly irregular is an arrhythmia that first appears to be irregular, but may actually include some regularity or pattern. The arrhythmia detection circuit 715 may detect AF when the measured Wenkebach regularity of the rhythm is less than a specified Wenkebach threshold. For instance, measuring the regularity may include determining one or both of similar maximum heart rate and similar minimum heart rate. The arrhythmia detection circuit 715 may look for a consecutive number of X-beat windows in the sensed cardiac signal, where X is a positive integer greater than one (e.g., 2, 3 . . . or 7 beat windows). Multiple different window sizes are applied to the sensed cardiac signal. The arrhythmia detection circuit 620 determines the highest percentage of X-beat windows with similar maximum heart rates (and/or similar minimum heart rates).

Table I is an illustrative example of window sizes of X=2 to 7 beats and a percentage of consecutive X-beat widows that had similar maximum or minimum heart rate. A "similar" maximum or minimum heart rate means that the max (or min) for a given window is within, as an example, +/−5 bpm of the previous window max (or min).

If any of the window sizes includes a fraction or percentage of maximum heart rate (or minimum heart rate) that exceeds the specified Wenckebach threshold, AF is not detected. If the fraction or percentage of maximum heart rate (and/or minimum heart rate) of all of the window sizes are less than the specified Wenckebach threshold, the arrhythmia detection circuit 715 detects AF.

TABLE I

| Window-size | % Max HR | % Min HR |
|---|---|---|
| 2 | 20% | 25% |
| 3 | 31% | 36% |
| 4 | 42% | 47% |
| 5 | 53% | 58% |
| 6 | 64% | 69% |
| 7 | 75% | 80% |

In the example of Table I, 20% of the consecutive 2-beat windows had a similar maximum heart rate and 25% had a similar minimum heart rate, and 75% of the consecutive 7-beat windows had similar maximum heart rates and 80% had similar minimum heart rates. If the Wenkebach threshold percentage is specified as 40%, the arrhythmia detection circuit 620 would not detect AF in the example. Any of window sizes 4 through 7 would negate a finding of AF because a repeating pattern is found for those window sizes that meets the Wenkebach detection criterion. The threshold fraction or percentage can be raised to make the detection more sensitive or lowered to make the detection more specific for AF detection. In response to detecting an oversensing event, the arrhythmia detection circuit 715 may decrease the Wenckebach threshold used to declare AF.

In another illustrative example of dynamic detection, either or both of the first and second detection criteria may include using an analysis of morphology of the sensed cardiac signal to detect AF. The arrhythmia detection circuit 715 may include a correlation circuit (not shown) that determines a score associated with correlation of the morphology of the sensed cardiac signal to the morphology of a template signal representative of AF. An example of a correlation score is a feature correlation coefficient (FCC). The FCC can provide an indication of a degree of similarity between the shape of the sensed electrogram and the shape of the template electrogram signal that represents AF. In variations, the template electrogram signal can represent normal sinus rhythm. The template may be recorded for a particular subject or may be created based on a patient population. The arrhythmia detection circuit 715 may detect AF when the determined score satisfies a specified AF detection threshold. The detection for AF can be adjusted to be more sensitive or less sensitive by adjusting the threshold score. In response to detecting an oversensing event, the arrhythmia detection circuit 715 may increase the threshold correlation score used to declare AF.

As indicated previously, undersensing by the sensing circuits of the device can result in false indications related to the detection of atrial tachyarrhythmia. The arrhythmia detection circuit 715 may determine that undersensing by the sensing circuit 710 is occurring when the device-determined heart rate of the patient or subject is non-physiologically slow. In another example, the arrhythmia detection circuit 715 may determine that undersensing is occurring when detecting a number of pauses in cardiac depolarization in the received cardiac signal that exceeds a specified threshold number of pauses. The pauses may indicate that the sensing circuits are sometimes missing detection of cardiac depolarization. In a further example, the arrhythmia detection circuit 715 may determine that undersensing is occurring when detecting a number of changes in amplitude of the received cardiac signal that exceed a specified amplitude change threshold within a specified period of time. As explained previously, some physiologic events can change the amplitude of cardiac signals. For instance, a posture change by the patient can reduce R-waves in a cardiac signal. This change in amplitude may trigger an adjustment of sensing thresholds in the device which may cause the sensing circuits to miss sensing events in the cardiac signal.

When undersensing is detected, the arrhythmia detection circuit 715 may change one or more thresholds of the first and second atrial tachyarrhythmia detection criteria. For instance, if the arrhythmia detection circuit 715 uses V-V dispersion for detection of AF and a suspected episode of AF is rejected with possible undersensing evident, the arrhythmia detection circuit 715 may increase the threshold of the measure of V-V dispersion to increase specificity of AF detection. In another example, if the arrhythmia detection circuit 715 uses V-V interval double decrement detection for detection AF, the arrhythmia detection circuit 715 may decrease the threshold for detection of V-V interval double decrementing to be more inclusive of AF in response to detecting an undersensing event. In another example, if the arrhythmia detection circuit 715 uses V-V interval Wenckebach detection for detection AF, the arrhythmia detection circuit 715 may decrease the Wenckebach threshold to increase specificity of AF. In a further example, if the arrhythmia detection circuit 715 uses a signal morphology analysis for detection AF, the arrhythmia detection circuit 715 may increase the threshold correlation score for AF, or decrease the correlation threshold score for NSR, to increase specificity of AF detection.

As indicated previously, the presence of confounding cardiac rhythms can result in false indications related to the detection of atrial tachyarrhythmia. These rhythms can include cardiac rhythms that appear to be irregular and disorganized, but which actually include some organization. The arrhythmia detection circuit 715 may detect these types of rhythms using Wenckebach detection approach or using histogram analysis to detect clusters of V-V interval values. Other confounding rhythms include PVCs or PACs. The arrhythmia detection circuit 715 may detect these types of rhythms using a morphology analysis.

When any of these type of cardiac rhythms are detected, the arrhythmia detection circuit 715 may change one or more thresholds of the first and second atrial tachyarrhythmia detection criteria. For instance, if the arrhythmia detection circuit 715 uses V-V dispersion for detection of AF, the arrhythmia detection circuit 715 may increase the threshold of the measure of V-V dispersion in the presence of the cardiac rhythm to increase specificity of AF detection. If the arrhythmia detection circuit 715 uses V-V interval double decrement detection for detection AF, the arrhythmia detection circuit 715 may increase the threshold for detection of V-V interval double decrementing to increase specificity to detection of AF. If the arrhythmia detection circuit 715 uses V-V interval Wenckebach detection for detection AF, the arrhythmia detection circuit 715 may decrease the Wenckebach threshold to increase specificity of AF. If the arrhythmia detection circuit 715 uses a signal morphology analysis for detection AF, the arrhythmia detection circuit 715 may decrease the correlation threshold score for NSR to increase specificity of AF detection.

Figure 10:
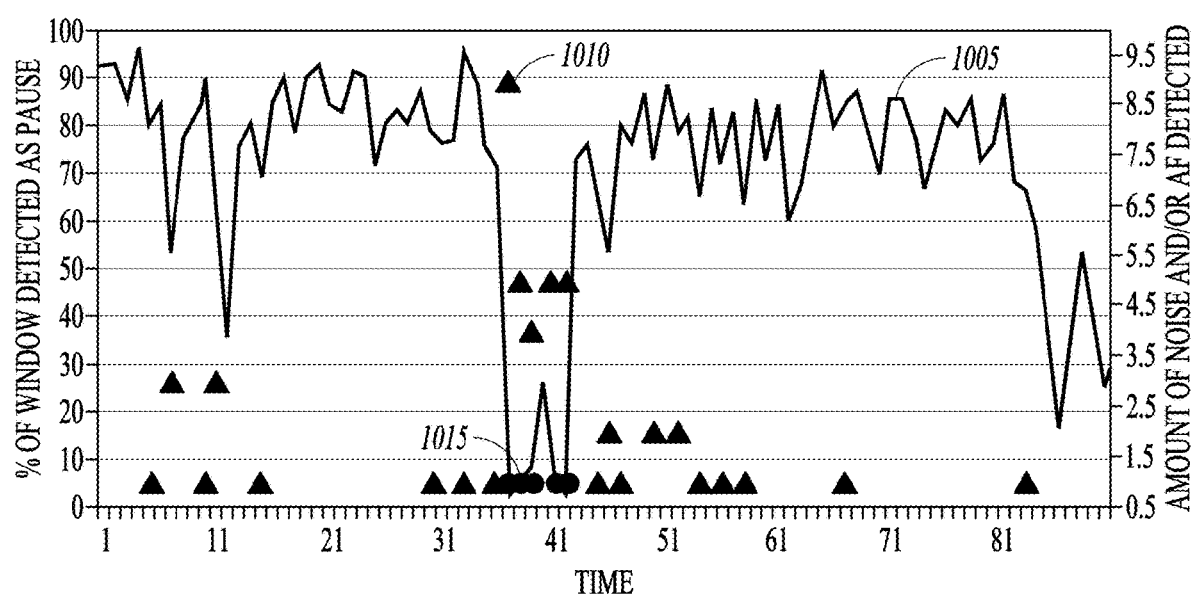
FIG. 10 is a graph showing false positives in detection of atrial fibrillation using an ambulatory medical device.

FIG. 10 is a graph showing false positives in detection of AF using a medical device. The horizontal axis shows detection windows timed by the device for detection of AF. The waveform 1005 is the percentage of heart beats during a detection window that were determined to include a pause. A high percentage of pauses may indicate undersensing by the medical device. The triangles 1010 indicate non-physiologically fast heart rates detected. Non-physiologically fast heart rates may indicate oversensing by the medical device. From time window 1 to about time window 35, and from about time window 41 to time window 81, there is a high percentage of pauses and non-physiologically fast heart rates are present. However, AF is not declared by the device during these time windows due to the high percentage of pauses and likely undersensing.

During the time period from about time window 35 to time window 41, the amount of undersensing drops and the device generates false positives of AF at 1015. Oversensing is present during widows 35 to 41, but the thresholds for AF detection are not set appropriately to prevent the false positives. The false positives could be avoided by the medical device automatically changing the detection thresholds to make it more difficult to declare AF when the sensing event is detected indicating susceptibility to false indications of atrial tacharrhythmia. The medical device may change the detection thresholds for a predetermined number of windows, or may change the detection thresholds until the sensing event is no longer detected.

Returning to FIG. 7, the ambulatory medical device 705 may include a therapy circuit 725 that can be electrically coupled to electrodes to provide an anti-arrhythmic cardiac therapy to the subject. The control circuit 720 may initiate delivery of an anti-arrhythmic therapy in response to an indication by the arrhythmia detection circuit 715 that atrial tachyarrhythmia such as AF is detected. In some examples, the therapy circuit 725 provides electrical pacing therapy to the subject. The control circuit 720 may initiate delivery of the electrical pacing therapy according to a first pacing therapy mode, and change the pacing therapy mode according to the detection of atrial tachyarrhythmia.

The previous examples have related to detection of atrial tachyarrhythmia, but the concepts can be applied to detection of other types of cardiac arrhythmia as well. According to some examples, the arrhythmia detection circuit 715 detects ventricular tachyarrhythmia by applying the first and second arrhythmia detection criteria to a sensed cardiac signal. Ventricular tachyarrhythmia can include ventricular fibrillation (VF) and ventricular tachycardia (VT). Some of the conditions that can result in false indications related to the detection of ventricular tachyarrhythmia include oversensing or undersensing by the sensing circuits. In response to detecting a sensing event that includes oversensing or undersensing, the arrhythmia detection circuit 715 may change one or more detection thresholds of the first and second detection criteria.

As an illustrative example of dynamic detection of ventricular tachyarrhythmia, the first or second arrhythmia detection criteria may include detecting ventricular tachyarrhythmia when detecting that a number of beats are fast beats, e.g., six out of ten beats are fast beats for a period of ten seconds. A heart beat may be declared a fast beat when the V-V interval is less than a specified fast beat interval. In response to detecting possible oversensing by the sensing circuit 710, the arrhythmia detection circuit may increase the threshold to eight of ten beats being used to detect ventricular tachyarrhythmia. In another example, the first or second arrhythmia detection criteria may include detecting ventricular tachyarrhythmia using heart rate stability. For instance, the arrhythmia detection circuit 715 may classify a rhythm as ventricular tachyarrhythmia if the heat rate of the patient is in a specified VF or VT heart rate zone and the V-V intervals indicate that the intervals are unstable. In response to detecting possible oversensing or undersensing, the arrhythmia detection circuit 715 may change a time threshold for the rhythm to be present before declaring ventricular tachyarrhythmia, or change the instability threshold to make it more difficult to classify a rhythm as ventricular tachyarrhythmia. In certain examples, the arrhythmia detection circuit 715 may add a morphology analysis to the detection process, such as by adding the morphology analysis to the second detection criteria.

Another condition that can result in false indications related to the detection of ventricular tachyarrhythmia includes the presence of a cardiac rhythm that confounds the detection of ventricular tachyarrhythmia. Some examples of a cardiac rhythm that confounds the detection of ventricular tachyarrhythmia include AT or AF. Similar to the response to undersensing or oversensing, when the arrhythmia detection circuit 715 is monitoring for ventricular tachyarrhythmia and detects AF or AT, the arrhythmia detection circuit 715 may change a time threshold for the rhythm to be present before declaring ventricular tachyarrhythmia, or change the instability threshold to make it more difficult to classify a rhythm as ventricular tachyarrhythmia.

The therapy circuit 725 may provide defibrillation shock therapy to the subject. The control circuit 720 initiates delivery of defibrillation shock therapy in response to VF or VT being detected. Because the arrhythmia detection circuit 715 may change a time threshold for the rhythm to be present before declaring VF or VT, the control circuit 720 may withhold the delivery longer in the presence of undersensing, oversensing, or in the presence of a confounding rhythm.

According to some examples, the arrhythmia detection circuit 715 detects bradycardia by applying the first and second arrhythmia detection criteria to a sensed cardiac signal. In response to detecting a sensing event that includes oversensing or undersensing, the arrhythmia detection circuit 715 may change one or more detection thresholds of the first and second detection criteria. For instance, the arrhythmia detection circuit 715 may change the dynamic sensing threshold response for the sensing circuit 710 to make detection of a pause more difficult. The therapy circuit 725 may provide electrical pacing therapy to the subject, and the control circuit initiates delivery of the electrical pacing therapy according to a first pacing therapy mode (e.g., a pacing mode defined according to the North American Society of Pacing and Electrophysiology, or NASPE). The control circuit 720 may change the pacing therapy mode according to the detected bradycardia of the patient.

Adaptive or dynamic classification of cardiac arrhythmia can improve detection in device-based cardiac monitoring of patients. False alarms by the devices can be reduced in the presence of conditions in which the risk of the false alarms increases. Correctly identifying cardiac arrhythmias can help to provide the most effective device-based therapy or non-device based therapy (e.g., drug therapy) for the patient.

Additional Description

The systems, devices, and methods discussed in this document may improve the medical technology of automated cardiac rhythm management (CRM) and detection and prevention of worsening of cardiac function. The heart rate-based arrhythmia detection may also enhance the performance and functionality of an implantable CRM device, in certain examples, increasing the efficacy of existing AF detection (e.g., by detecting the true onset of AF), such that system performance can be improved with little to no additional cost, while reducing manual inspection required for such detection. In other examples, existing system performance can be maintained (e.g., high AF sensitivity and specificity, etc.) using lower cost or less obtrusive systems, apparatus, and methods. For example, because the system or device does not require direct atrial activity sensing for atrial arrhythmias detection, the system complexity and implementation cost may be reduced. It may particularly be beneficial for patient not indicated for atrial lead implantation either for atrial activity sensing or for atrial pacing. The device-based arrhythmia detection also allows for more efficient use of device memory, such as by correctly storing heart rate statistics that are clinically relevant to arrhythmia recognition. Because onset of AF is more accurately reported, fewer unnecessary drugs and procedures can be scheduled, prescribed, or provided, and the overall management of the patient's cardiac disease can be improved.

The above detailed description includes references to the accompanying drawings, which form a part of the detailed description. The drawings show, by way of illustration, specific embodiments in which the invention can be practiced. These embodiments are also referred to herein as "examples." All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code can form portions of computer program products. Further, the code can be tangibly stored on one or more volatile or non-volatile computer-readable media during execution or at other times. These computer-readable media can include, but are not limited to, hard disks, removable magnetic disks, removable optical disks (e.g., compact disks and digital video disks), magnetic cassettes, memory cards or sticks, random access memories (RAM's), read only memories (ROM's), and the like. In some examples, a carrier medium can carry code implementing the methods. The term "carrier medium" can be used to represent carrier waves on which code is transmitted.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

What is claimed is:

1. An apparatus of an ambulatory medical device, the apparatus comprising:
   an arrhythmia detection circuit including signal processing circuitry configured to:
   receive a cardiac signal representative of cardiac activity;
   apply an atrial arrhythmia detection criteria to the received cardiac signal;
   apply, in response to the applied atrial arrhythmia detection criteria producing a positive indication of a type of arrhythmia, an atrial arrhythmia confirmation criteria to the received cardiac signal, wherein the atrial arrhythmia confirmation criteria is different from the atrial arrhythmia detection criteria and is more specific to detection of the type of arrhythmia detected than the atrial arrhythmia detection criteria;
   detect a sensing event that causes false indications of detection of arrhythmia by one or both of the atrial arrhythmia detection criteria and the atrial arrhythmia confirmation criteria; and
   adjust the sensitivity or specificity of the atrial arrhythmia detection criteria and the atrial arrhythmia confirmation criteria in response to detecting one or more of a number of pauses in cardiac depolarization in the received cardiac signal that exceeds a specified threshold number of pauses, a heart rate that is non-physiologically slow, and a number of changes in amplitude of the received cardiac signal that exceed a specified amplitude change threshold within a specified period of time.

2. The apparatus of claim 1, wherein the arrhythmia detection circuit is configured to adjust the sensitivity or specificity of the atrial arrhythmia detection criteria and the atrial arrhythmia confirmation criteria in response to detection of one or both of a heart rate that is non-physiologically fast, and a specified number of noise hits in sensing of the cardiac signal that occur within a specified time duration.

3. The apparatus of claim 1, wherein the arrhythmia detection circuit is configured to adjust the sensitivity or specificity of the atrial arrhythmia detection criteria and the atrial arrhythmia confirmation criteria in response to detection of a cardiac rhythm for which one or both of the atrial arrhythmia detection criteria and the atrial arrhythmia confirmation criteria are susceptible to false alarms.

4. The apparatus of claim 1, wherein the arrhythmia detection circuit is configured to detect atrial tachyarrhythmia using the atrial arrhythmia detection criteria and the atrial arrhythmia confirmation criteria; adjust a detection threshold of the arrhythmia detection criteria and the atrial arrhythmia confirmation criteria to change sensitivity or specificity to atrial tachyarrhythmia detection in response to detection of the sensing event, and restore the detection threshold to an original sensitivity or specificity when the detected sensing event ceases to be detected for a specified period of time.

5. The apparatus of claim 4, wherein the arrhythmia detection circuit is configured to detect atrial flutter (AF) using the atrial arrhythmia detection criteria and the atrial arrhythmia confirmation criteria, wherein the arrhythmia detection criteria and the atrial arrhythmia confirmation criteria include one or more of: detection that sensed ventricular depolarization intervals (V-V intervals) satisfy a specified V-V interval scatter AF detection threshold, detection that sensed V-V intervals satisfy a specified V-V interval double decrement AF detection threshold, and detection that sensed V-V intervals satisfy a specified Wenckebach AF detection threshold.

6. The apparatus of claim 1, wherein the arrhythmia detection circuit is configured to: detect ventricular tachyarrhythmia using the atrial arrhythmia detection criteria and the atrial arrhythmia confirmation criteria;
adjust a detection threshold of one or both of the and atrial arrhythmia detection criteria to change sensitivity or specificity to ventricular tachyarrhythmia detection in response to detection of the sensing event; and restore the detection threshold to an original sensitivity or specificity when the detected sensing event ceases to be detected for a specified period of time.

7. The apparatus of claim 6, including:
a therapy circuit configured to provide defibrillation shock therapy to the subject; and
a control circuit configured to initiate delivery of the defibrillation shock therapy in response to the detection of the ventricular tachyarrhythmia.

8. The apparatus of claim 1, wherein the arrhythmia detection circuit is configured to: detect bradycardia using the atrial arrhythmia detection criteria and the atrial arrhythmia confirmation criteria; adjust a detection threshold of one or both of the and atrial arrhythmia detection criteria to change sensitivity or specificity to bradycardia detection in response to detection of the sensing event; and restore the detection thresholds to an original specificity when the detected sensing event ceases to be detected for a specified period of time.

9. The apparatus of claim 8, including:
a therapy circuit configured to provide electrical pacing therapy to the subject; and
a control circuit configured to initiate delivery of the electrical pacing therapy according to a first pacing therapy mode; and change the pacing therapy mode according to the detected cardiac arrhythmia.

10. The apparatus of claim 1, wherein the arrhythmia detection circuit is configured to continue to adjust the sensitivity or specificity of the atrial arrhythmia detection criteria and the atrial arrhythmia confirmation criteria when continuing to detect the sensing event, and restore original sensitivity or specificity to the atrial arrhythmia detection criteria and the atrial arrhythmia confirmation criteria when the detected sensing event ceases to be detected for a specified period of time.

11. A method of controlling operation of an arrhythmia detection circuit, the method comprising:
receiving a cardiac signal representative of electrical cardiac activity at the arrhythmia detection circuit;
applying an arrhythmia detection criteria to the received cardiac signal using the arrhythmia detection circuit;
applying, in response to the applied atrial arrhythmia detection criteria producing a positive indication of a type of arrhythmia, an atrial arrhythmia confirmation criteria to the received cardiac signal using the arrhythmia detection circuit, wherein the atrial arrhythmia confirmation criteria is different from the atrial arrhythmia detection criteria and is more specific to detection of the type of arrhythmia detected than the atrial arrhythmia detection criteria;
detecting, using the arrhythmia detection circuit, a sensing event that causes false indications of detection of arrhythmia by one or both of the atrial arrhythmia detection criteria and the second atrial arrhythmia confirmation criteria, wherein the detecting the sensing event includes one or more of detecting a number of pauses in cardiac depolarization in the sensed cardiac signal, detecting a heart rate that is non-physiologically slow, and sensing a specified number of changes in amplitude of the sensed cardiac signal that exceed a specified amplitude change threshold within a specified period of time; and
adjusting, in response to the detected sensing event, sensitivity or specificity of the atrial arrhythmia detection criteria and the atrial arrhythmia confirmation criteria using the arrhythmia detection circuit.

12. The method of claim 11, wherein the detecting the sensing event includes one or both of:
detecting a specified number of noise hits in the sensing of the cardiac signal within a specified time duration, and
detecting a heart rate that is non-physiologically fast.

13. The method of claim 11, wherein the detecting the sensing event includes detecting a cardiac rhythm for which one or both of the atrial arrhythmia detection criteria and the atrial arrhythmia confirmation criteria are susceptible to false alarms.

14. The method of claim 11, wherein the atrial arrhythmia detection criteria and the atrial arrhythmia confirmation criteria detect atrial tachyarrhythmia, wherein the adjusting sensitivity or specificity includes adjusting an atrial tachyarrhythmia detection threshold of one or both of the atrial arrhythmia detection criteria and the atrial arrhythmia confirmation criteria, and wherein the method further includes restoring the atrial tachyarrhythmia detection threshold to an original sensitivity or specificity when the detected sensing event ceases to be detected for a specified period of time.

15. A system comprising:
a sensing circuit configured to provide a sensed ventricular cardiac signal of a subject when operatively coupled to electrodes that contact a subject; and
an arrhythmia detection circuit operatively coupled to the sensing circuit and configured to:
apply a atrial arrhythmia detection criteria to the sensed ventricular cardiac signal;
apply, in response to the applied atrial arrhythmia detection criteria producing a positive indication of atrial arrhythmia, a atrial arrhythmia confirmation criteria to the sensed ventricular cardiac signal, wherein the arrhythmia confirmation criteria is different from the criteria and is more specific to detection of atrial arrhythmia than the atrial arrhythmia detection criteria;

detect a sensing event that causes false indications of detection of arrhythmia by one or both of the and atrial arrhythmia detection criteria, wherein the sensing event includes one or more of detecting a number of pauses in cardiac depolarization in the sensed cardiac signal, detecting a heart rate that is non-physiologically slow, and sensing a specified number of changes in amplitude of the sensed cardiac signal that exceed a specified amplitude change threshold within a specified period of time; and adjust, in response to the detected sensing event, sensitivity or specificity of the atrial arrhythmia detection criteria and the atrial arrhythmia confirmation criteria.

16. The system of claim 15, wherein the arrhythmia detection circuit is configured to detect atrial flutter (AF) using the atrial arrhythmia detection criteria and the atrial arrhythmia confirmation criteria, adjust a detection threshold of one or both of the detection criteria and the atrial arrhythmia confirmation criteria to change sensitivity or specificity to AF in response to detection of the sensing event, and restore the detection threshold to an original sensitivity or specificity when the detected sensing event ceases to be detected for a specified period of time.

17. The system of claim 16, wherein the arrhythmia detection circuit is configured to:
confirm AF using the atrial arrhythmia confirmation criteria when sensed ventricular depolarization intervals (V-V intervals) satisfy one or more of a specified V-V interval scatter AF detection threshold, a specified V-V interval double decrement AF detection threshold, and a specified Wenckebach AF detection threshold; and
change the sensitivity or specificity of the one or more of the V-V interval scatter AF detection threshold, the V-V interval double decrement AF detection threshold, and the Wenckebach AF detection threshold in response to detection of the sensing event.

18. The system of claim 15, wherein the arrhythmia detection circuit is configured to includes restoring the atrial arrhythmia detection threshold to an original sensitivity or specificity when the detected sensing event ceases to be detected for a specified period of time.

19. The system of claim 15, including:
a therapy circuit configured to provide electrical pacing therapy to the subject; and
a control circuit configured to initiate delivery of the electrical pacing therapy according to a pacing therapy mode; and change the pacing therapy to a different pacing therapy mode according to the detected cardiac arrhythmia.

20. The method of claim 11, including:
delivering electrical pacing therapy according to a pacing therapy mode; and
changing the pacing therapy mode according to the detected cardiac arrhythmia.

* * * * *